US005686095A

United States Patent [19]

Price, Jr.

[11] Patent Number: 5,686,095
[45] Date of Patent: Nov. 11, 1997

[54] METHOD OF TREATING CANKER SORES

[76] Inventor: Francis W. Price, Jr., 5511 Sunset La., Indianapolis, Ind. 46208

[21] Appl. No.: 546,740

[22] Filed: Oct. 23, 1995

[51] Int. Cl.$^6$ .................. A61K 31/435; A61K 31/495
[52] U.S. Cl. ................. 424/435; 424/78.02; 514/230.2; 514/255; 514/299; 514/928
[58] Field of Search ................... 424/484; 514/928, 514/255, 299

[56] References Cited

U.S. PATENT DOCUMENTS

| | | | |
|---|---|---|---|
| 3,923,984 | 12/1975 | Zuercher | 424/195 |
| 4,117,120 | 9/1978 | Elderbaum | 424/195 |
| 4,191,750 | 3/1980 | Hodosh | 424/127 |
| 4,229,430 | 10/1980 | Fahim et al. | 424/49 |
| 4,443,607 | 4/1984 | Senda et al. | 546/141 |
| 4,466,956 | 8/1984 | Leeds | 424/80 |
| 4,551,456 | 11/1985 | Katz | 514/254 |
| 4,777,253 | 10/1988 | Mitscher et al. | 544/101 |
| 4,826,985 | 5/1989 | Mitscher et al. | 546/156 |
| 4,868,192 | 9/1989 | Totten et al. | 514/928 |
| 4,895,944 | 1/1990 | Havakawa et al. | 544/105 |
| 4,923,862 | 5/1990 | Hirota | 514/230.2 |
| 4,965,262 | 10/1990 | Kametaka et al. | 514/230.2 |
| 5,051,509 | 9/1991 | Nagano et al. | 546/156 |
| 5,128,489 | 7/1992 | Kumobavashi et al. | 549/419 |
| 5,142,046 | 8/1992 | Hayakawa et al. | 544/105 |
| 5,179,096 | 1/1993 | Gentilini et al. | 514/253 |
| 5,182,104 | 1/1993 | Marcus et al. | 424/78.07 |
| 5,227,372 | 7/1993 | Folkman | 514/58 |
| 5,288,503 | 2/1994 | Woop et al. | 424/497 |
| 5,401,741 | 3/1995 | Sato et al. | 514/230.2 |
| 5,438,075 | 8/1995 | Skubitz et al. | 514/563 |

OTHER PUBLICATIONS

Legwold, Gary, "Small Medical Problems", *Better Homes and Gardens*, Aug. 1994, p. 46.

Stokes, R.W., Koprince, D., "Recurrent Aphthous Stomatitis: Review of the literature"; *Journal of Am. Osteopath Assoc.* (USA), 1982, 81/11 (pp. 776–781).

*Primary Examiner*—Peter F. Kulkosky
*Attorney, Agent, or Firm*—Woodard, Emhardt, Naughton, Moriarty & McNett

[57] ABSTRACT

A method of treating canker sores is disclosed by which a fluoroquinolone is topically applied to the ulcerous area. The fluoroquinolone is shown to be applied in solution form, and also as a paste, ointment, or gel. The fluoroquinolone is preferably applied three to eight times a day until the lesion disappears.

22 Claims, No Drawings

METHOD OF TREATING CANKER SORES

FIELD OF THE INVENTION

The present invention relates to the field of medical science. More particularly, the present invention relates to methods of treating canker sores.

BACKGROUND TO THE INVENTION

Canker sores (also known as aphthous ulcerations or recurrent aphthae) are painful sores which form in the mucus membrane of the mouth. Many people experience the pain and discomfort of this common affliction. The sores first appear as small red lesions which quickly whiten and then break down to form shallow ulcers. Each sore may last for up to two weeks, with the sores generally lasting for seven to ten days. In severe attacks, the sores can be especially painful, making it difficult to eat or speak.

While the cause of canker sores has not been identified, emotional stress has been associated with the condition. Although a wide variety of treatments have been tried and suggested, the results have been generally disappointing. A need continues to exist for a new method for treating this common, painful affliction which is reliably effective, and the present invention addresses that need.

SUMMARY OF THE INVENTION

The present invention provides a new and effective method of treating canker sores by which a fluoroquinolone composition is administered to the ulcerous area. In one preferred embodiment, the fluoroquinolone is applied in solution form. Other forms of treatment are also shown and described, wherein the fluoroquinolone is topically applied in the form of a paste, ointment, or gel. The fluoroquinolone is preferably applied topically three to eight times a day until the lesion disappears.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the preferred embodiments, and such further applications of the principles of the invention as described herein being contemplated as would normally occur to one skilled in the art to which the invention pertains.

According to the present invention, canker sores are treated by the administration of a fluoroquinolone composition. In one preferred embodiment, the sores are treated by topically applying a solution of fluoroquinolone directly to the affected area. The fluoroquinolone is preferably applied three to eight times daily until the sores disappear, with the treatment generally only being necessary for a period of two or three days. This is a significant improvement over prior art methods which typically require seven to ten days of treatment.

Fluoroquinolones useful for practicing the present invention include that entire class of synthetic compounds derived from nalidixic acid. Examples of therapeutically useful fluoroquinolone compounds include of ioxacin, ciprofloxacin and norfloxacin. These compounds are commercially available under the trade names Ocuflox® (ofloxacin), Cil-oxan® (ciprofloxacin) and Chibroxin® (norfloxacin).

Fluoroquinolones useful for practicing the present invention may be described by the following chemical formulation:

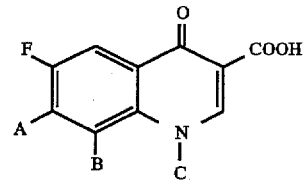

A is

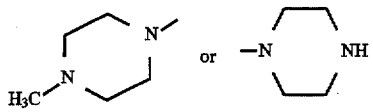

B is H or a lower (e.g., $C_1$–$C_8$) alkyl; and
C is $C_2H_5$ or

In one embodiment, B and C jointly comprise

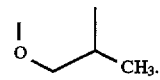

As mentioned above, the fluoroquinolone is preferably applied topically to the ulcerous area. Fluoroquinolones have been topically applied in solution form with successful results. The fluoroquinolone may be applied topically in other forms as well, such as in a paste, ointment, or gel. Alternatively, the fluoroquinolone may be ingested orally or injected. Topical treatment is generally preferred, however, because lower doses may be used while still obtaining a satisfactory concentration of fluoroquinolone at the ulcer site, thus minimizing the potential for side effects which may result from systemic administration.

Dosage levels are generally controllable by selecting the concentration and amount of the fluoroquinolone composition to be applied. When a dilute (0.3%) solution is used, for example, an appropriate dosage may be obtained by applying between about one and three drops of solution to the lesion. Generally, a dosage sufficient to bathe the entire lesion in solution is appropriate, although excess quantities of fluoroquinolone should be avoided. To facilitate application to the various regions within the mouth where canker sores occur, the solution may be applied with a curved dropper. Alternatively, a common, straight dropper or other solution applicator may also be used.

Reference will now be made to specific examples of the methods described above. It is to be understood that the examples are provided to more completely describe the preferred embodiments, and that no limitation to the scope of the invention is intended thereby.

EXAMPLE 1

A patient with an aphthous ulcer is treated by topically applying a 0.3% solution of ofloxacin directly to the lesion. The ofloxacin is applied three times daily for a period of about three days. By the end of the three-day treatment cycle, the lesion has healed.

EXAMPLE 2

A patient with an aphthous ulcer is treated by topically applying a 0.3% solution of ciprofloxacin directly to the lesion. The ciprofloxacin is applied eight times daily for a period of two days. By the end of the two-day treatment cycle, the lesion has healed.

EXAMPLE 3

A patient with an aphthous ulcer is treated by topically applying a 0.3% solution of norfloxacin directly to the lesion. The norfloxacin is applied four times daily for a period of three days. By the end of the three-day treatment cycle, the lesion has healed.

EXAMPLE 4

A patient with an aphthous ulcer is treated by topically applying a paste of 0.1% ofloxacin directly to the lesion. The ciprofloxacin is applied three times daily for a period of three days. By the end of the three-day treatment cycle, the lesion has healed.

EXAMPLE 5

A patient with an aphthous ulcer is treated by topically applying an ointment of 0.1% ciprofloxacin directly to the lesion. The ciprofloxacin is applied four times daily for a period of three days. By the end of the three-day treatment cycle, the lesion has healed.

EXAMPLE 6

A patient with an aphthous ulcer is treated by topically applying a gel of 0.1% norfloxacin directly to the lesion. The ciprofloxacin is applied six times daily for a period of three days. By the end of the three-day treatment cycle, the lesion has healed.

While the invention has been illustrated and described in detail in the foregoing description, the same is to be considered as illustrative and not restrictive in character, it being understood that only the preferred embodiments have been shown and described, and that all changes and modifications that come within the spirit of the invention are desired to be protected.

What is claimed is:

1. A method of treating aphthous ulcerations, said method comprising the step of administering a composition of fluoroquinolone to the ulceration.

2. The method of claim 1 wherein said fluoroquinolone is ofloxacin.

3. The method of claim 1 wherein said fluoroquinolone is ciprofloxacin.

4. The method of claim 1 wherein said fluoroquinolone is norfloxacin.

5. The method of claim 1 wherein said fluoroquinolone is administered by topically applying the composition to the ulceration site.

6. The method of claim 1 wherein said fluoroquinolone is administered by topically applying a fluoroquinolone solution to the ulceration site.

7. The method of claim 6 wherein said fluoroquinolone solution has a concentration of about 0.3%.

8. The method of claim 5 wherein said fluoroquinolone is applied in the form of a paste.

9. The method of claim 5 wherein said fluoroquinolone is applied in the form of an ointment.

10. The method of claim 5 wherein said fluoroquinolone is applied in the form of a gel.

11. A method of treating apthous ulcerations, said method comprising the step of administering to the ulceration a composition of the formula:

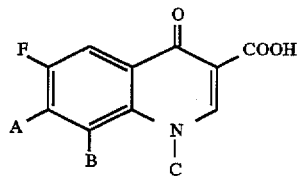

where
A is

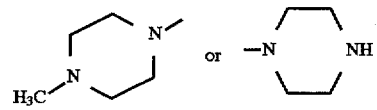

B is H or a lower (e.g., $C_1$–$C_8$) alkyl; and
C is $C_2H_5$ or

12. The method of claim 11 wherein said composition is administered by topically applying said composition to the ulceration site.

13. The method of claim 11 wherein said composition is administered by topically applying a solution of said composition to the ulceration site.

14. The method of claim 12 wherein said composition is applied in the form of a paste.

15. The method of claim 13 wherein said composition is applied in the form of an ointment.

16. The method of claim 14 wherein said composition is applied in the form of a gel.

17. A method of treating apthous ulcerations, said method comprising the step of administering to the ulceration a composition of the formula:

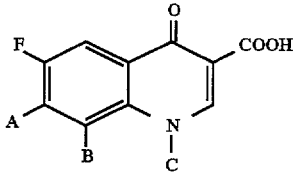

where
A is

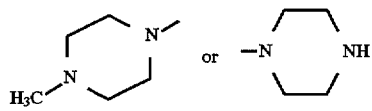

and
B and C jointly comprise

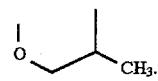

18. The method of claim 17 wherein said composition is administered by topically applying said composition to the ulceration site.

19. The method of claim 17 wherein said composition is administered by topically applying a solution of said composition to the ulceration site.

20. The method of claim 18 wherein said composition is applied in the form of a paste.

21. The method of claim 18 wherein said composition is applied in the form of an ointment.

22. The method of claim 18 wherein said composition is applied in the form of a gel.

* * * * *

UNITED STATES PATENT AND TRADEMARK OFFICE
CERTIFICATE OF CORRECTION

PATENT NO : 5,686,095

DATED : November 11, 1997

INVENTOR(S): Francis W. Price, Jr.

It is certified that error appears in the above-identified patent and that said Letters Patent is hereby corrected as shown below:

In column 1, line 64, please change "of ioxacin" to --ofloxacin--.

In column 2, line 13, please insert the word "where" at the beginning of the line (before the words "A is").

Signed and Sealed this

First Day of December, 1998

Attest:

Attesting Officer

BRUCE LEHMAN

Commissioner of Patents and Trademarks